(12) United States Patent
Wakamatsu et al.

(10) Patent No.: US 7,677,087 B2
(45) Date of Patent: Mar. 16, 2010

(54) QUARTZ SENSOR AND SENSING DEVICE

(75) Inventors: Shunichi Wakamatsu, Sayama (JP); Mitsuaki Koyama, Sayama (JP); Tsuyoshi Shiobara, Sayama (JP)

(73) Assignee: Nihon Dempa Kogyo Co., Ltd., Tokyo (JP)

( * ) Notice: Subject to any disclaimer, the term of this patent is extended or adjusted under 35 U.S.C. 154(b) by 59 days.

(21) Appl. No.: 11/792,966

(22) PCT Filed: Dec. 14, 2005

(86) PCT No.: PCT/JP2005/023421

§ 371 (c)(1),
(2), (4) Date: Sep. 10, 2007

(87) PCT Pub. No.: WO2006/064954

PCT Pub. Date: Jun. 22, 2006

(65) Prior Publication Data

US 2008/0134767 A1    Jun. 12, 2008

(30) Foreign Application Priority Data

Dec. 15, 2004   (JP) ............................. 2004-363516

(51) Int. Cl.
G01N 29/028 (2006.01)
G01N 29/032 (2006.01)
G01N 29/036 (2006.01)

(52) U.S. Cl. .................... 73/64.53; 73/54.41; 73/61.49; 73/61.75

(58) Field of Classification Search ............... 73/61.79, 73/24.01–24.06, 61.43–61.49, 61.71, 61.75, 73/54.41, 64.53; 310/361, 311
See application file for complete search history.

(56) References Cited

U.S. PATENT DOCUMENTS

| | | | | |
|---|---|---|---|---|
| 4,213,104 A | * | 7/1980 | Cullen et al. | 333/150 |
| 4,312,228 A | * | 1/1982 | Wohltjen | 73/597 |
| 4,471,259 A | * | 9/1984 | Stoermer et al. | 310/353 |
| 4,639,631 A | * | 1/1987 | Chason et al. | 310/344 |
| 4,991,283 A | | 2/1991 | Johnson et al. | |
| 5,196,347 A | | 3/1993 | Kaneko et al. | |
| 5,211,054 A | * | 5/1993 | Muramatsu et al. | 73/64.42 |
| 5,494,639 A | | 2/1996 | Grzegorzewski | |

(Continued)

FOREIGN PATENT DOCUMENTS

JP    1-244335    9/1989

(Continued)

*Primary Examiner*—David A. Rogers
(74) *Attorney, Agent, or Firm*—Jordan and Hamburg LLP

(57) ABSTRACT

Provided is a Angevin type quartz sensor which is high in measurement sensitivity, suppresses the influence of the surface tension of a sample solution during measurement, and enables an installed quartz resonator to stable oscillate. An opposing surface portion opposes one surface side of the quartz resonator via a housing area and a pouring opening formed in the outside area of the opposing surface portion. Measurement is conducted in a standstill state where the sample solution is filled in the lower side of the opposing surface portion. Since stress due to the surface tension of the sample solution does not act in this state, the quartz resonator can oscillate with reliability. Therefore, the quartz sensor can reduced the thickness of the quartz resonator, which realizes highly sensitive and highly accurate measurement.

5 Claims, 10 Drawing Sheets

U.S. PATENT DOCUMENTS

| | | | |
|---|---|---|---|
| 5,892,143 A | 4/1999 | Namerikawa et al. | |
| 6,156,578 A * | 12/2000 | Tom | 436/149 |
| 6,210,226 B1 | 4/2001 | Zhu et al. | |
| 6,321,588 B1 | 11/2001 | Bowers et al. | |
| 6,525,549 B1 | 2/2003 | Poellmann | |
| 7,075,216 B1 * | 7/2006 | Vetelino | 310/338 |
| 2004/0016297 A1 | 1/2004 | Paul et al. | |
| 2004/0187580 A1 | 9/2004 | Nozaki | |
| 2004/0194548 A1 * | 10/2004 | Dayagi et al. | 73/580 |
| 2005/0069864 A1 * | 3/2005 | Itoh et al. | 435/4 |
| 2005/0082944 A1 * | 4/2005 | Thompson et al. | 310/318 |
| 2006/0272396 A1 * | 12/2006 | Itoh et al. | 73/64.53 |
| 2006/0277978 A1 * | 12/2006 | Jakoby et al. | 73/54.02 |

FOREIGN PATENT DOCUMENTS

| | | |
|---|---|---|
| JP | 3-188350 | 8/1991 |
| JP | 3-257346 | 11/1991 |
| JP | 4-1554 | 1/1992 |
| JP | 4-9744 | 1/1992 |
| JP | 5-5735 | 1/1993 |
| JP | 7-190916 | 7/1995 |
| JP | 7-190919 | 7/1995 |
| JP | 9-145583 | 6/1997 |
| JP | 9-250936 | 9/1997 |
| JP | 10-038788 | 2/1998 |
| JP | 10-142134 | 5/1998 |
| JP | 10-332463 | 12/1998 |
| JP | 11-183479 | 7/1999 |
| JP | 2000-338022 | 12/2000 |
| JP | 2001-83154 | 3/2001 |
| JP | 2001-099777 | 4/2001 |
| JP | 2001-201436 | 7/2001 |
| JP | 2002-148295 | 5/2002 |
| JP | 2002-243607 | 8/2002 |
| JP | 2004-506194 | 2/2004 |
| JP | 2004-205392 | 7/2004 |
| JP | 2004-264254 | 9/2004 |
| JP | 2005-43123 | 2/2005 |

* cited by examiner

| 101 | THE FIRST AREA |
| 102 | THE SECOND AREA |
| 103 | THE THIRD AREA |
| 2 | QUARTZ RESONATOR |

PRIOR ART

QUARTZ SENSOR AND SENSING DEVICE

TECHNICAL FIELD

The present invention relates to a quartz sensor utilizing a Langevin type quartz resonator which is composed such that one surface of a quartz piece comes in contact with a measurement medium and the other surface faces an airtight space to sense an object to be detected by detecting variation in frequency, and to a sensing device using the quartz sensor.

BACKGROUND ART

A measuring method that uses a sensing device equipped with a quartz sensor using a quartz resonator for sensing a substance in minute quantities such as an environmental pollutant e.g. dioxin or the like, or a disease marker for the hepatitis C virus, a C-reactive protein (CRP), or the like has been widely known.

To be more specific, the measurement method is conducted in such a manner that an adsorbing layer is formed in advance on an excitation electrode on one surface side of the quartz resonator, and the presence/absence of the object to be measured or the concentration thereof in a sample solution is measured by applying a property that when the object is adsorbed, the resonance frequency of the quartz piece varies according to the mass of the adsorbed substance. In Patent Document 1, there is a description that for the purpose that the quartz resonator equipped in the quartz sensor used in this measurement method be oscillated in a stable fashion in an immuno-latex solution, it is desirable to have a structure in which only one surface of the quartz resonator comes in contact with a measurement medium.

Such a quartz sensor is usually called a Langevin type quartz resonator. Though not described in Patent Document 1, the fundamental structure of the Langevin type quartz resonator generally has a composition shown in FIG. 11. 10 in the drawing is a round quartz piece, and foil-shaped electrodes 11 and 12 are respectively formed at the center of both surfaces. Supporting line members 13 and 14 to take out an electric signal outside, lead wires of, for instance about 0.5 mm in diameter are connected to these electrodes 11 and 12. A base 16 having a recess 15 is placed on the other surface side of the quartz piece 10. The quartz piece 10 and the base 16 are adhered firmly by an adhesive 17, thereby forming an airtight space enclosed by the quartz piece 10 and the recess 15.

In recent years, further control of toxic substances which have a large effect on an environment such as the above-described dioxin or the like that has been demanded from the viewpoint of environmental protection, and attempts to achieve measurement in the ppt level have been widely conducted. In a quartz resonator, the resonance frequency of the quartz resonator increases as the thickness of the quartz piece decreases. From the Sauerbrey equation, the greater the frequency generated by the quartz resonator, the more the amount of deviation in frequency in regard to the amount of change in mass of the object. In other words, when the quartz piece becomes thinner and thinner, the measurement sensitivity of the quartz sensor increases, so that the measurement of a substance in minute quantities becomes possible. Therefore, reduction in the thickness of the quartz piece is required.

The technology to reduce the layer thickness of a quartz piece has progressed at present, and it has become possible to manufacture a quartz piece with a thickness of several to several tens of μm. When a quartz resonator is composed using this thin layered quartz piece, however, the quartz resonator easily receives the influence of surface tension of the sample solution to be measured, and there is a possibility of not causing oscillation owing to the surface tension or not generating oscillation due to stabilization. When liquid 10B drops down on a plane, it rounds in a convex shape due to the surface tension as shown in FIG. 12A, and in a recess, the liquid surface is curved in a concave shape as shown in FIG. 12B, which generates a stress acting on the plane due to the surface tension. Accordingly, when a quartz resonator 10A is arranged in the plane portion in FIG. 12A or a bottom portion in FIG. 12B, a stress acts on the quartz resonator 10A. Accordingly, in the structure shown in FIG. 11, a stress acts on the quartz resonator 10A in a manner shown by the arrow due to the surface tension of the sample solution. If a housing area for the sample solution is taken widely, the effect of the surface tension can be reduced, but it causes the quartz sensor upsize. Therefore, it is practically inevitable for the quartz resonator 10A to avoid influence of the surface tension of the sample solution, and if reduction in thickness of the quartz piece progresses, the influence of the stress applied on the quartz piece in regard to the deviation in the natural frequency becomes large, and sometimes it would not oscillate anymore.

In Patent Document 2, there is a description of technology of the Langevin type quartz sensor. The technology includes the step of forming a passage space for a sample solution on one surface side of the quartz resonator and supplying the sample solution from an inflow opening to conduct measurement while flowing out the sample solution from an outflow opening. Since, however, the method of flowing the sample solution in this manner causes a large stress on the thin-layered quartz piece, such a structure cannot be adopted at all, and the structure to solve the surface tension issue is not shown.

Patent Document 1: Japanese Patent Application Laid-open No. 2001-83154 (paragraph 0009, paragraph 0019 and FIG. 1)

Patent Document 2: Japanese Patent Application Laid-open No. Hei 11-183479 (paragraph 0024, FIG. 3 and FIG. 10)

DISCLOSURE OF THE INVENTION

The problem of the present invention is to resolve the above-described disadvantages of the conventional technology, and an object of the present invention is to provide a Langevin type quartz sensor and a sensing device which is high in measurement sensitivity, and influence of the surface tension of the sample solution during measurement can be suppressed so that the quartz resonator can oscillate in a stable fashion.

A quartz sensor of the present invention used for detecting an object to be measured in the sample solution, comprising:

a member provided with a recess for forming an airtight space;

a quartz resonator held by the above-described member in a state that excitation electrodes are equipped respectively on one surface side and the other surface side of a quartz piece of the quartz resonator and the excitation electrode on the other surface side covers the recess so as to face the above-described airtight space;

an adsorbing layer which is provided on the excitation electrode on the one surface side and adsorbs the object to be measured in the sample solution;

a housing area forming portion which encloses the upper space above the one surface side of the above-described quartz resonator and for forming the housing area of the sample solution;

an opposing surface portion which faces the one face side of the above-described quartz resonator via the housing area, and is larger than the excitation electrode of the quartz resonator; and a pouring opening which is formed in the outside area of the opposing surface portion and for pouring the sample solution into the above-described housing area, wherein the object is measured based on the variation in the natural frequency of the quartz resonator caused by adsorption of the object to be measured on an adsorbing layer, and the measurement is conducted in a standstill state that the sample solution is filled in the lower side of the opposing surface portion.

That the standstill state in which the sample solution is filled in the lower side of the opposing surface portion means a state that the liquid surface level at the pouring opening is above the opposing surface portion and no space exists in the lower side of the opposing surface portion.

The above-described quartz sensor may be provided with a confirmation opening that connects to the housing area at the position different from the above-described pouring opening, and to confirm the liquid surface level of the sample solution. In addition, for instance, the equivalent thickness of the quartz piece is thinner than 200 μm. A sensing device relating to another invention includes a quartz sensor of the present invention, and a measurement device main unit to detect the presence or absence of the object to be measured and/or the concentration thereof by detecting the variation in the natural frequency of the quartz sensor.

According to the present invention, in a quartz sensor using a Langevin type quartz resonator in which an adsorbing layer for adsorbing the object to be measured in the sample solution is formed on the one surface side, an opposing surface portion larger than the excitation electrode of the quartz resonator is provided, and measurement is conducted in a state that the sample solution is filled between this opposing surface portion and the excitation electrode. Accordingly, the liquid surface of the sample solution above the excitation electrode is in contact with the opposing surface portion, which results in no generation of surface tension. Accordingly, since no stress caused by the surface tension of the sample solution acts on the excitation electrode, the quartz resonator oscillates with reliability, and since it oscillates at the frequency corresponding to the amount of adsorption of the object to be measured, it is possible to conduct measurement at high accuracy. As described above, it is necessary for improvement of the measurement sensitivity to increase the frequency of the quartz resonator, which results in reduction in thickness of the quartz resonator. Then, the measurement receives a great influence even with a slight stress. Therefore, the present invention is able to realize highly sensitive and highly accurate measurement (detection of the presence or absence of the object to be measured and measurement of the concentration thereof).

BEST MODE FOR CARRYING OUT THE INVENTION

Figure 1:
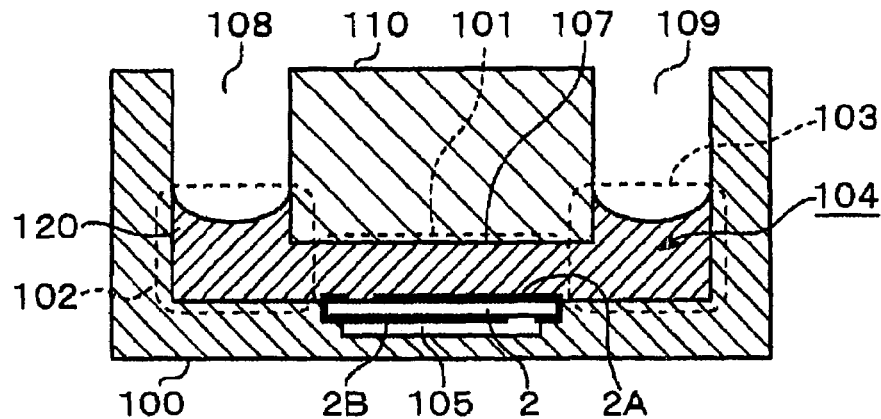
FIG. 1 is an explanatory view showing a principal structure of a quartz sensor relating to the present invention.

The embodiments of the present invention will be explained hereinafter. In order to make understanding of the gist of the embodiment easy, the basic structure of a principal portion of a quartz sensor relating to the present invention will be explained first with reference to FIG. 1. The quartz sensor is provided with housing area forming portions 100 and 110 for a sample solution. A recess 104 is formed in the housing area forming portion 100, and at the bottom surface of the recess 104, a recess 105 for forming an airtight space is formed. A quartz resonator 2 is provided so as to cover the recess 105, and an excitation electrode 2B on the other surface side of the quartz resonator 2 faces an airtight space which is a space in the recess 105.

The recess 104 includes a first area 101 having a space for the whole excitation electrode 2A on one surface side of the quartz resonator 2, a second area 102 and a third area 103 respectively formed on both sides of the first area 101 being adjacent to the first area 101. The first area 101 serves as a measurement area where a sample solution 120 is in contact with the quartz resonator 2, and above the first area 101, the housing area 110 larger than the excitation electrode 2A of the quartz resonator 2, in this example an opposing surface portion 107 which is larger than the quartz resonator 2, is provided, so that the excitation electrode 2A is housed within a projection area of the opposing surface portion 107.

The recess 104 containing the first area 101, the second area 102 and the third area 103 corresponds to a housing area (pouring space). The upper surface sides of the second area 102 and the third area 103 are connected to the outside of the quartz sensor via holes 108 and 109 respectively, and the hole 108 on the upper surface side of the second area 102 is formed as a pouring opening for pouring the sample solution 120 into the above-described pouring space of the sample solution. The hole 109 on the upper surface side of the third area is preferably formed of as, for instance, a confirmation opening (detection opening) of the sample solution 120 as will be described in detail in an embodiment to be described later.

Though it is possible to form the housing area forming portion 100 and 110 out of an integrated member, they are composed of members separated into a quartz holding member and a lid as shown in an embodiment to be described later for instance.

In the case of forming the principal portion of the quartz sensor in this manner, when the sample solution 120 is filled in the first area 101 and kept in a standstill state as shown in the drawing, generation of the surface tension of the sample solution 120 is suppressed in this area. Therefore, it is possible to oscillate the quartz resonator 2 in a stable fashion.

FIRST EMBODIMENT

Figure 2:
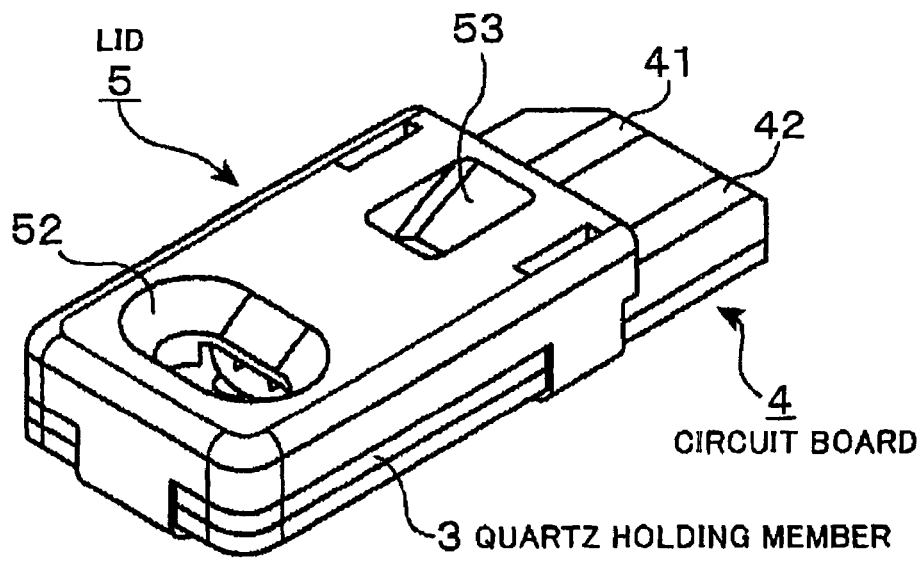
FIG. 2 is a perspective view showing an embodiment of the quartz sensor relating to the present invention.
Figure 3:
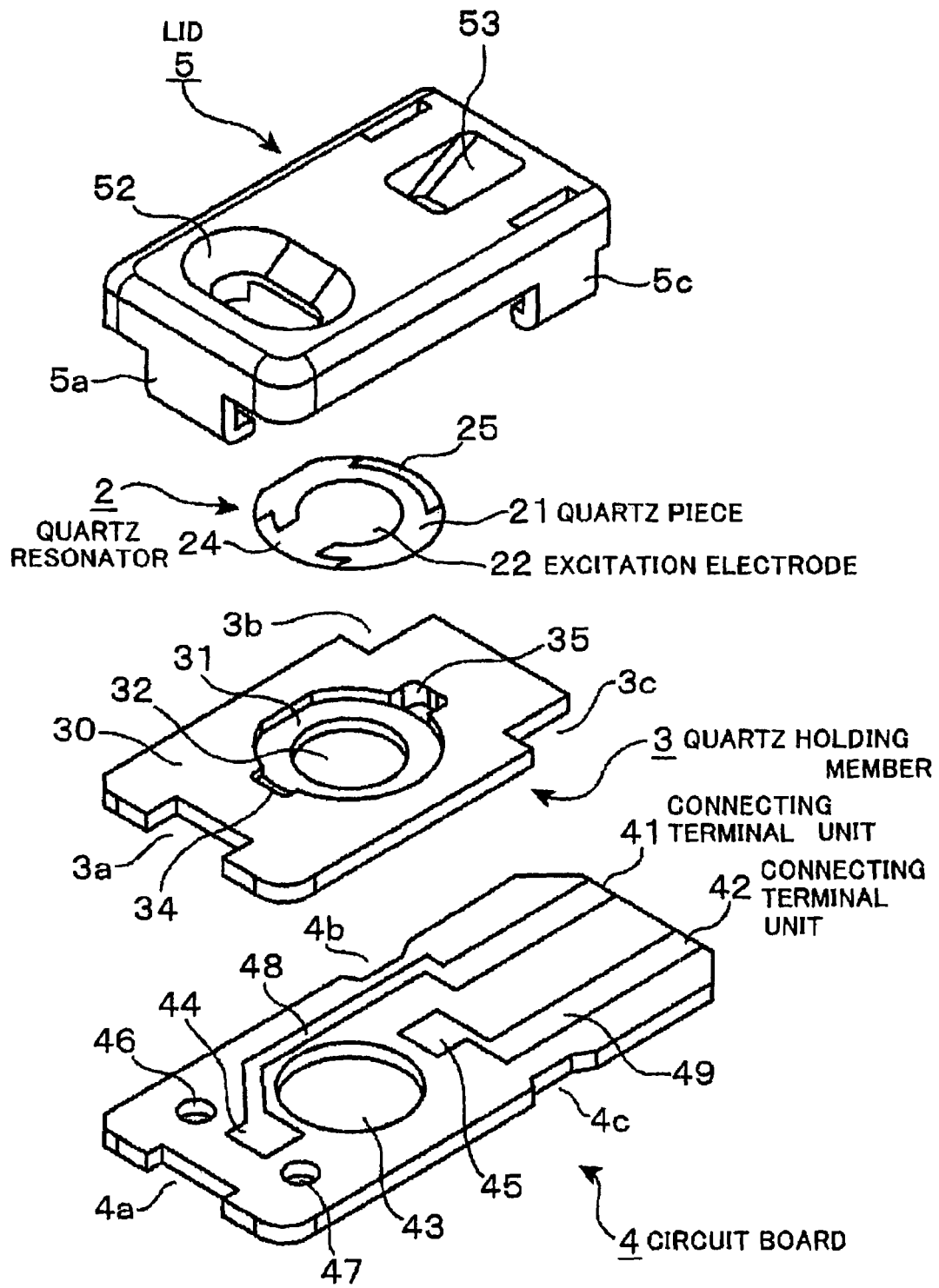
FIG. 3 is an exploded perspective view showing the upper surface of respective parts of the above-described quartz sensor.

The first embodiment of the quartz sensor relating to the present invention will be explained using FIG. 2 to FIG. 5. FIG. 2 is a perspective view showing an example of the quartz sensor relating to the present invention. The quartz sensor is structured by placing one upon another composed of the respective parts of a circuit board 4, a quartz holding member 3, a quartz resonator 2 and a lid 5 in this order from the bottom. FIG. 3 is a exploded perspective view showing the upper surface sides of the respective parts of the quartz sensor.

The quartz resonator 2 includes a quartz piece 21, excitation electrodes 22 and 23, and derivation electrodes 24 and 25. The quartz piece 21 has an equivalent thickness of 1 $\mu$m to 300 $\mu$m, preferably 185 $\mu$m, and is formed in a plate in which a portion of the periphery is cut off straight. On one surface side and the other surface side of the quartz piece 21, one foil-shaped excitation electrode 22 and the other foil-shaped excitation electrode 23 are stacked respectively and formed in a disk having a smaller diameter than the quartz piece 21. On one surface side of the quartz piece 21, an end of the foil-shaped derivation electrode 24 is connected to the excitation electrode 22, and the derivation electrode 24 is bent along the edge of the quartz piece 21, and turned back on the other surface side of the quartz piece. These excitation electrodes 22, 23 and the derivation electrodes 24, 25 serve as resonator electrodes.

In addition, on the other surface side of the quartz piece 21, the end of the other foil-shaped derivation electrode 25 is connected to the other excitation electrode 23 in a similar layout to that of the previously described derivation electrode 24, and the layouts of the excitation electrode 22 (23) and the derivation electrode 24 (25) are the same as each other on both surfaces of the quartz piece 21.

The equivalent thickness of the excitation electrodes 21, 22 and the derivation electrodes 23, 24 is, for instance, 0.2 $\mu$m, and though gold or silver is suitable for the material for the electrode, gold is more suitable because of high stability of frequency in a fluid, and the resistance against oxidation of the electrode surface during preservation in the air before use. An antibody or the like which is an adsorbing layer that selectively adsorbs an object, for instance dioxin, with the quartz sensor, is stuck on one surface side of the quartz resonator 2 in advance.

The quartz holding member 3 holding the quartz resonator 2 is made of a rubber sheet with a thickness of, for instance, 1 mm, and is formed in a shape matching for the circuit board 4 which will be described later. That is, the quartz holding member 3 is formed in a shape in which a rectangular notch 3a is formed in the center of one end on the front side of a rectangular body, and rectangular notches 3b and 3c are formed respectively at both corners on the rear side. Note that though rubber is preferable for the material for the quartz holding member 3, other elastic material can also be used. A recess 31 is formed on one surface side of the quartz holding member 3 in a form to be a similar figure to the shape of the quartz resonator 2 so that the quartz resonator 2 can be easily placed in the recess 31. As for the size, it is formed in a size substantially similar to the size of the quartz resonator 2, for instance, in a size similar to or a little larger than the quartz resonator 2. At the portion outside of the recess 31, through holes 34 and 35 which serve as spaces for applying a conductive adhesive to be described later are drilled so as to face each other on the outside of the recess 31. It should be noted that the depth of the recess 31 is designed to be a little greater than the thickness of the quartz resonator 2. In the bottom center of the recess 31, a round recess 32 which matches with the size of the excitation electrode 23 and forms an airtight atmosphere coming into contact with the excitation electrode 23 is formed.

The circuit board 4 will be explained next. The circuit board 4 is composed of, for instance, printed circuit boards, and an electrode 44, a round hole 43 matching with a round projection 33 projecting from the back surface side of the quartz holding member 3, and an electrode 45 are formed in this order from the front end side toward a rear end side. Two conductive path patterns in parallel lines are formed as connecting terminal units 41 and 42 respectively at a little to the rear end side from the position where the electrode 45 is formed. The one connecting terminal unit 41 is electrically connected to the electrode 44 via a pattern 48, and the other connecting terminal unit 42 is electrically connected to the electrode 45 via a pattern 49. Holes 46 and 47 are engaging holes to engage with engaging projections 36 and 37 (refer to FIG. 4) of the quartz holding member 3. The quartz holding member 3 is fixed on the circuit board 4 in a state that the front surface of the circuit board 4 and the back surface of the quartz holding member 3 are kept in absolute contact with one another by inserting the projection 33 projecting toward back surface side of the above-described quartz holding member 3 into the hole 43 of the circuit board 4, and at the same time by fitting (engaging) engaging projections 36 and 37 of the quartz holding member 3 into the engaging holes 46 and 47 of the circuit board 4. At this time, a portion of or the whole of the electrodes 44 and 45 are exposed in the upper surface via the holes 34 and 35 of the quartz holding member 3.

Figure 4:
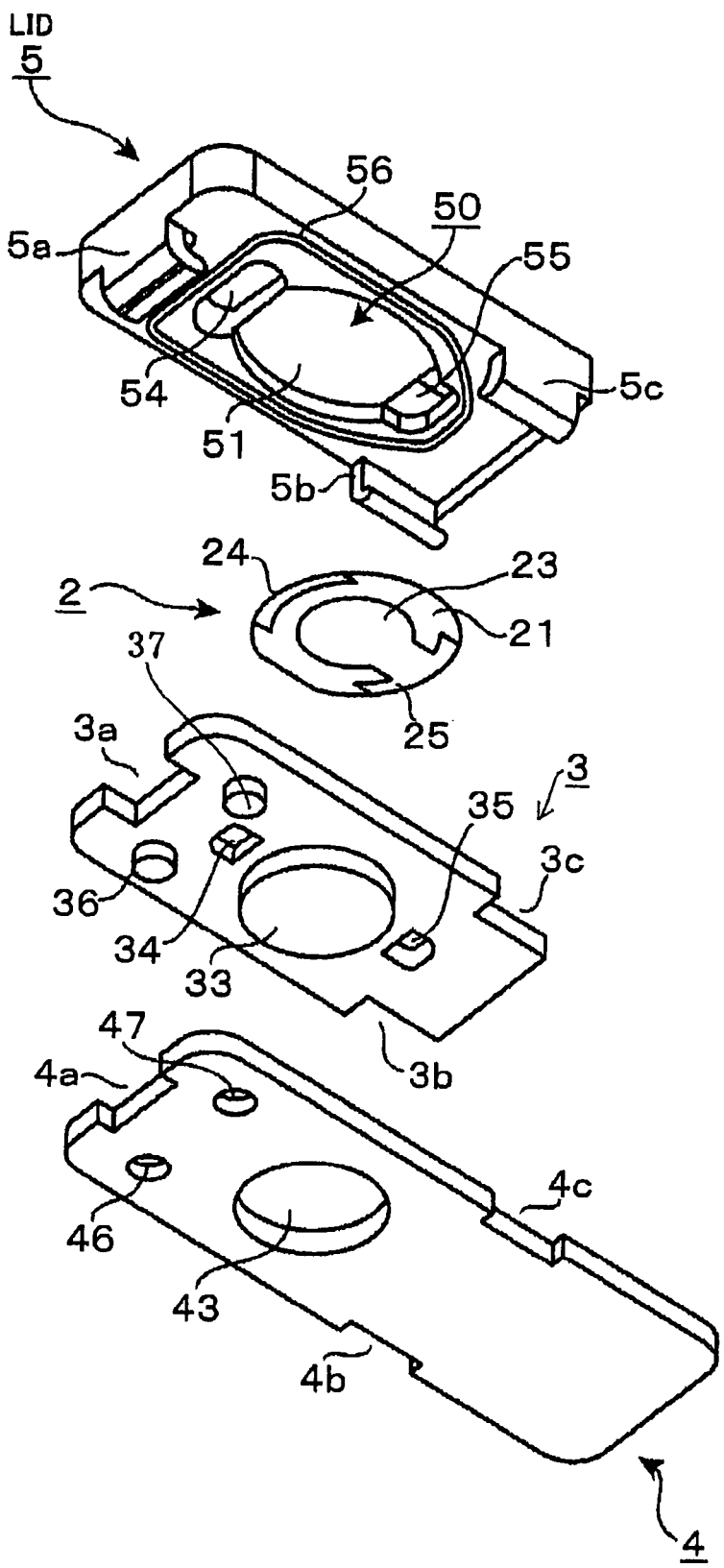
FIG. 4 is an exploded perspective view showing the lower surface of respective parts of the above-described quartz sensor.
Figure 5:
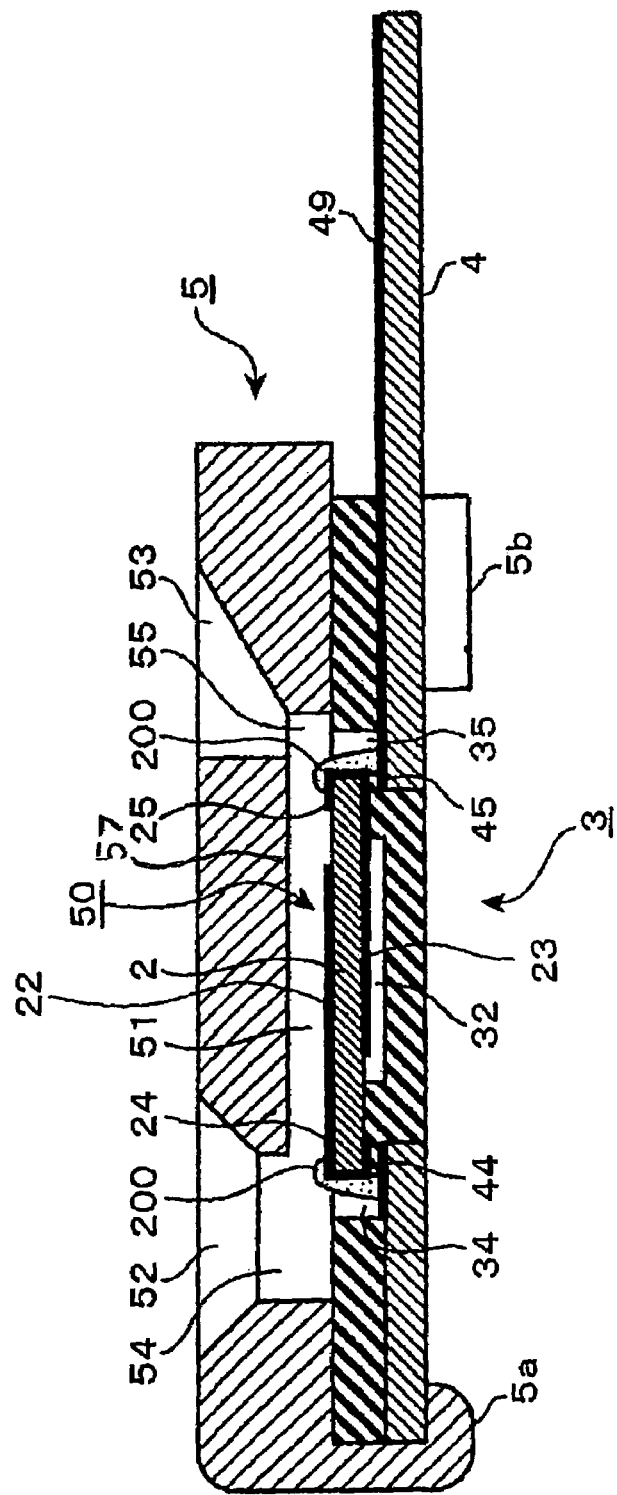
FIG. 5 is a vertical cross sectional view of the quartz sensor.

The structure of the lid 5 will be explained next. The lid 5 has a recess 50 formed on the back surface side as shown in FIG. 4. The recess 50 includes a first area 51 having a space enclosing the whole of the recess 32 in the quartz holding member 3, a second area 54 and a third area 55 respectively formed both in front and in the rear of the first area 51, as shown in FIG. 4 and FIG. 5. The first area 51 serves as a measurement area where the sample solution comes into contact with the quartz resonator 2, and an opposing surface 57 having a size equal to or larger than the excitation electrode 22 of the quartz resonator 2 is arranged on the upper surface of the first area 51 so that the excitation electrode 22 is to be housed within the projection area in the opposing surface 57. The second area 54 and the third area 55 respectively extend above the holes 34 and 35 for applying a conductive adhesive in the quartz holding member 3, and an pouring opening 52 and a confirmation opening (detection opening) 53 for the sample solution are respectively formed on the upper surface side. That is, the pouring opening 52 and the confirmation opening 53 are positioned at a level higher than the opposing surface 57. The recess 50 including the first area 51, the second area 54 and the third area 55 corresponds to a pouring space, and the bottom surface of the peripheral portion surrounding the recess 50, in other words, the inside surface of the lid 5, serves as a pressing surface (close contact surface) which comes in close contact with a surface surrounding the quartz resonator 2 in the quartz holding member 3 and presses it. A rib 56 is provided in the inside surface of the lid 5 so as to surround the pressing surface.

The pouring opening 52 is formed in a manner that the bore thereof is increasing gradually from inside of the lid 5 to the upper surface of the lid 5, in other words, the inside of the pouring opening 52 is formed in a slope, for the purpose of pouring of the sample solution easier. The confirmation opening 53 is formed to have a slope portion milder in inclination than the slope of the confirmation opening 53 from inside of the lid 5 toward the rear end side of the upper surface of the lid 5 so that the water level appeared in the confirmation opening 53 is easy to be observed. Note that the confirmation opening 53 is formed so that the slope portion is exposed when the lid 5 is seen from the upper surface.

The quartz sensor having such a structure like this is assembled as follows. As described previously, the quartz holding member 3 is fitted into the circuit board 4, and the quartz resonator 2 is installed on the recess 36 of the quartz holding member 3 so that the quartz resonator 2 is fitted in the recess 36. Then, a conductive adhesive 200 is supplied from above the quartz holding member 3 using a dispenser or the like so that the derivation electrode 24 (25) of the quartz resonator 2 and the electrode 46 (48) of the circuit board 4 are electrically connected to each other via the hole 38 (39). The quartz resonator 2 is firmly fixed on the quartz holding member 3 by the conductive adhesive 200. Thus, an airtight space (space in the recess 36) is formed on the bottom surface side of the quartz resonator 2, and the Langevin type quartz sensor is composed.

Next, the assembly of the circuit board 4 and the quartz holding member 3 is covered with the lid 5 from the upper surface thereof so as to fit respective claws 5a, 5b and 5c into respective notch portions 4a, 4b and 4c, and is pressed toward the substrate. Then, the respective claws 5a, 5b and 5c formed on the lid 5 are bent toward the outside of the circuit board 4, and further the respective claws 5a, 5b and 5c come around the bottom surface of the peripheral portion of the circuit board 4 via the respective notch portions 4a, 4b and 4c. At the same time, the respective claws 5a, 5b and 5c are restored to their original shapes owing to the restoring force toward inside, so that the circuit board 4 is locked together by being caught with the respective claws 5a, 5b and 5c. The above-described pressing surface inside the lid 5 comes in close contact with the upper surface of the quartz holding member 3 to form the pouring space for the sample solution. In order to prevent impurities coming from the pouring opening 52 and the confirmation opening 53 from sticking to the quarts resonator 2 before measurement, the pouring opening 52 and the confirmation opening 53 are covered with a protective sheet in a film (not shown).

When the quartz sensor in the present embodiment is used, a predetermined quantity of the sample solution is poured into the second area 54 using an injector via the pouring opening 52 of the lid 5 by an operator, and a surface of the quartz resonator 2 comes in contact with a measurement medium by further pouring of the sample solution into the first area 51. At this time, blocked by a rib 56 stuck in the quartz holding member 3 on the lid 5, leakage of the sample solution from a gap between the lid 5 and the quartz holding member 3 into the outside of the quartz sensor is prevented with further reliability. The sample solution flowed into the first area 51 also flows into the third area 55. When the sample solution is continued to be poured, the water level of the sample solution rises at each area, and when the sample solution is filled in the first area 51, the surface tension disappears at this area. Accordingly, since the stress generated by the surface tension of the sample solution does not act on the excitation electrode 22 of the quartz resonator 2, the quartz resonator 2 oscillates without fail, and oscillates at the frequency corresponding to the amount of adsorption of the object to be measured. Therefore, measurement with high accuracy can be performed. In order to enhance the measurement sensitivity, it is necessary to increase the frequency of the quartz resonator as described above, which reduces the thickness of the quartz resonator, and exerts large influence on the measurement even with a slight stress. Therefore, the present invention is able to realize measurement (detection of the presence or absence of a measurement target or concentration measurement thereof) with high sensitivity and accuracy.

From above, the present invention is considered to be effective especially when the natural frequency of the quartz resonator is 8.3 MHz or more, that is, when the equivalent thickness of a quartz piece is 200 μm or less, the present invention is, however, not limited to such a condition.

When the sample solution fills the first area, the liquid level of the sample solution in the third area arrives at the confirmation opening 53 and the sample solution is still continued to be added, the liquid level goes up along the slope formed on the confirmation opening 53. Thereby, it becomes possible to easily confirm that the sample solution has been poured in the quartz sensor and the sample solution is filled in the first area 51 from outside of the quartz sensor.

Figure 6:
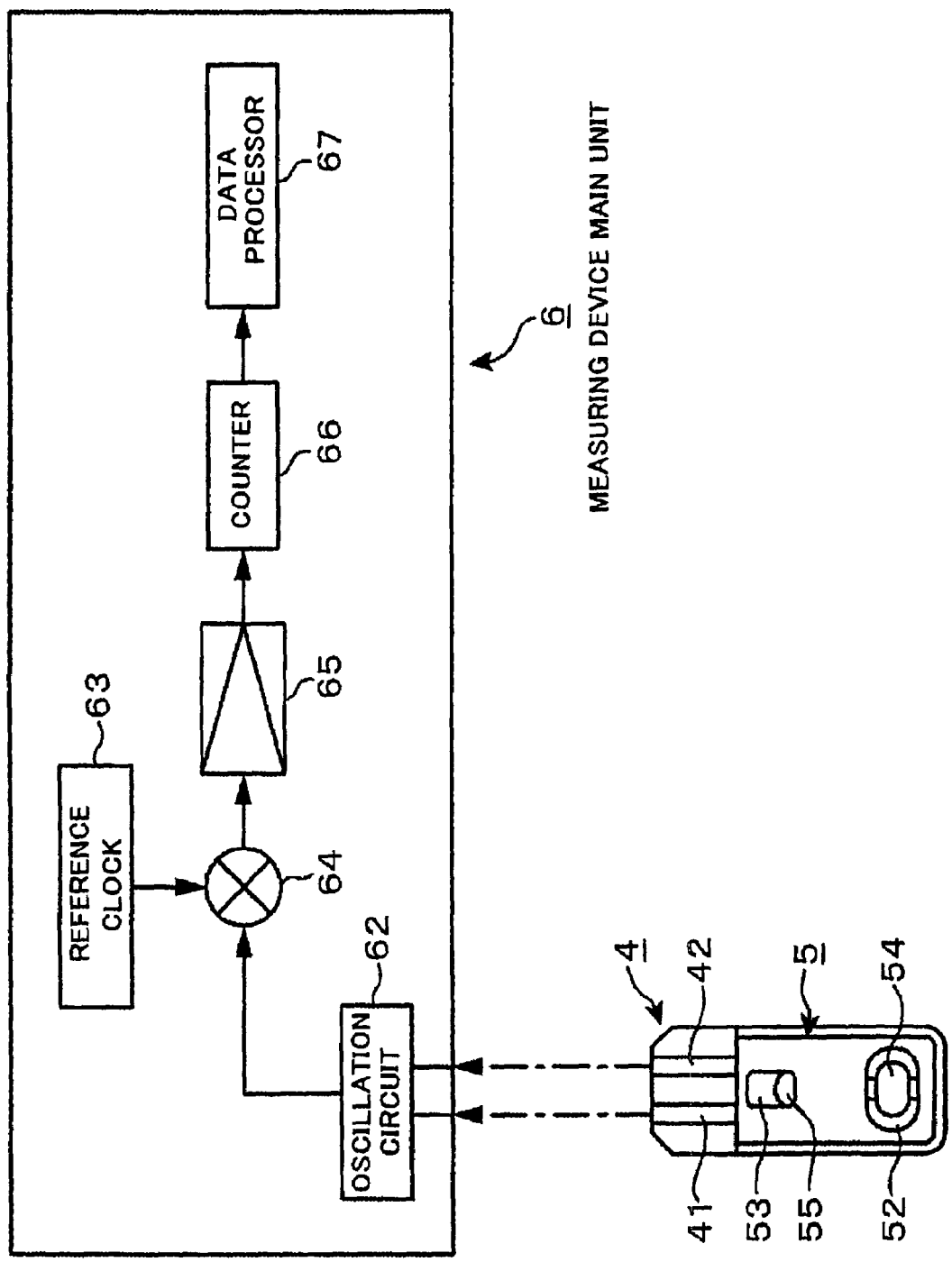
FIG. 6 is a block diagram showing a structural example of a measurement device main unit to which the quartz sensor relating to the present invention is connected.

Here, the quartz sensor is used as a sensor of a sensing device by connecting to a measuring device main unit 6 having a structure shown by, for instance, a block diagram FIG. 6. 62 in the drawing is an oscillating circuit for oscillating the quartz piece 21 of the quartz sensor, 63 is a reference clock generator for generating a reference frequency signal, 64 is a frequency difference detector composed of, for instance, a heterodyne wave detector and captures a frequency signal corresponding to the frequency difference between the oscillating circuit 62 and the reference clock generator 63 based on the frequency signal from the oscillation circuit 62 and the clock signal from the reference clock generator 63, 65 is an amplifier, 66 is a counter for counting the frequency of an output signal from the amplifier 65, 67 is data processor.

For instance, 9 MHz is selected as the frequency of the quartz sensor, and 10 MHz is selected as the frequency of the reference clock generator 53. When an object to be detected, for instance, dioxin, is not adsorbed to the quartz resonator 2 held in the quartz sensor, the frequency difference detector 64 outputs the frequency signal (frequency difference signal) of 1 MHz, that is the difference between the frequency from the quartz sensor and the frequency from the reference clock, but when the object to be detected (for instance, dioxin) contained in the sample solution is adsorbed to the quartz resonator 2, since the natural frequency varies and the frequency difference signal varies on this account, the count value also varies at the counter 66. Then, the concentration or presence/absence of the object to be measured can be detected by preparing in advance a calibration curve on variation of frequency (variation of count value) and concentration of the object to be measured (for instance, dioxin) in the sample solution.

Figure 7A:
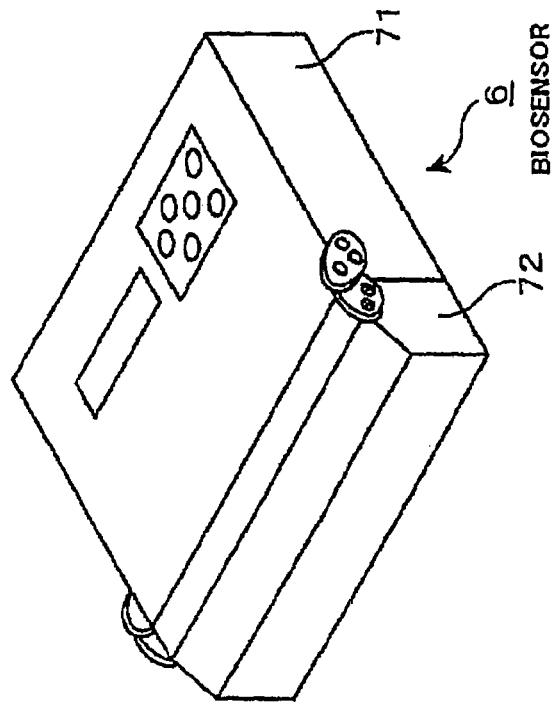
FIGS. 7A and 7B are perspective views showing a biosensor which is an example of the above-described measurement device main unit.
Figure 7B:
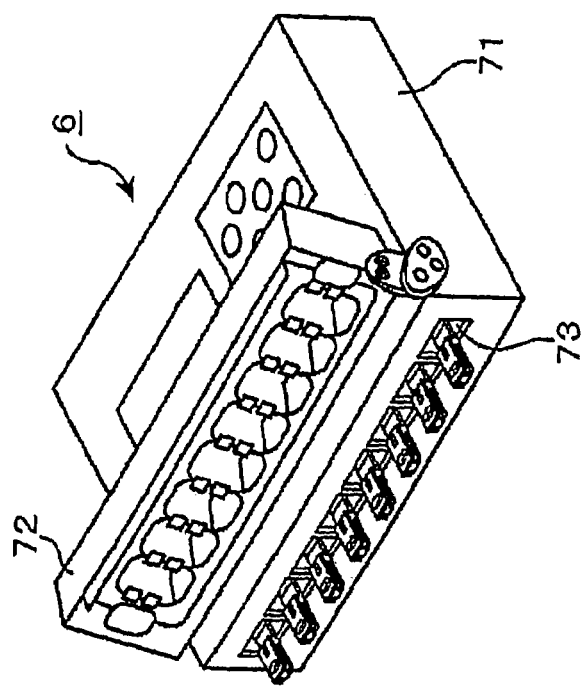

FIGS. 7A and 7B are views showing an example of the above-described measuring device main unit 6. As shown in FIG. 7A, the measuring device main unit 6 includes a main unit 71 and a retractable lid 72 formed in front of the main unit 71. When the lid 72 is opened, the front surface of the main unit 71 is appeared as shown in FIG. 7B. A plurality of plugs 73 of the quartz sensor is provided in front of the main unit 71, and the plural plugs 73 (for instance, 8 plugs) are formed in a straight line at fixed intervals.

The connecting terminal units 41 and 42 of the circuit board 4 and electrodes formed in the plugs 73 are electrically connected by horizontally inserting the rear end side of the circuit board 40 of the respective quartz sensors into the respective plugs 73 of the measuring device main unit 6 till the predetermined depth, and at the same time, the quartz sensors are firmly fixed to the measuring device main unit 6 while the quartz sensors are kept horizontally by sandwiching the circuit board 4 by the insides of the plugs 73. Since this structure makes it possible to directly connect it to the measuring device main unit 6 without using a special attachment, the wiring is not routed around on the measurement table, so that the measurement work is easily performed.

Figure 8A:
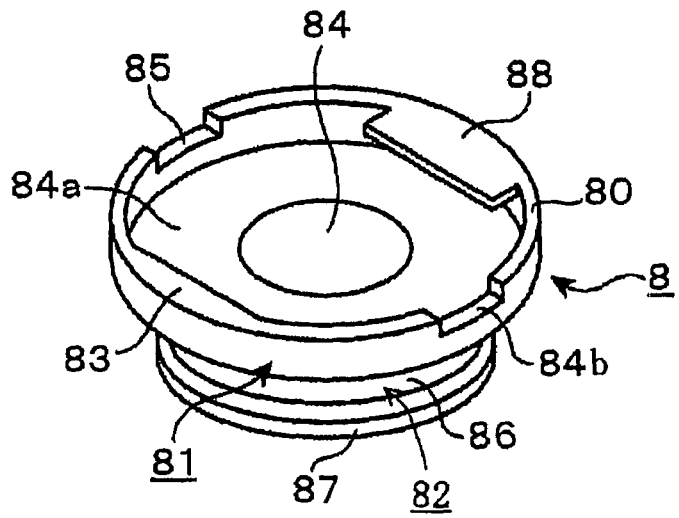
FIGS. 8A, 8B and 8C are explanatory views showing an example of a ring-shaped quartz holding member used for a quartz sensor relating to another embodiment.
Figure 8B:
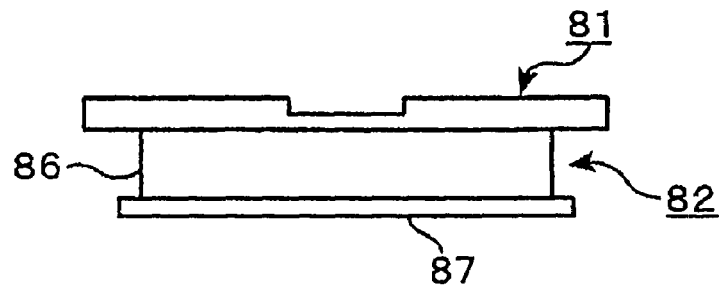
Figure 8C:
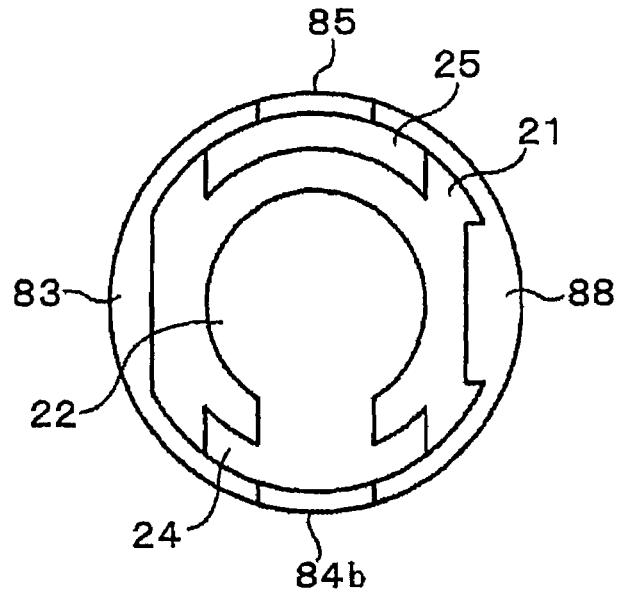
Figure 9A:
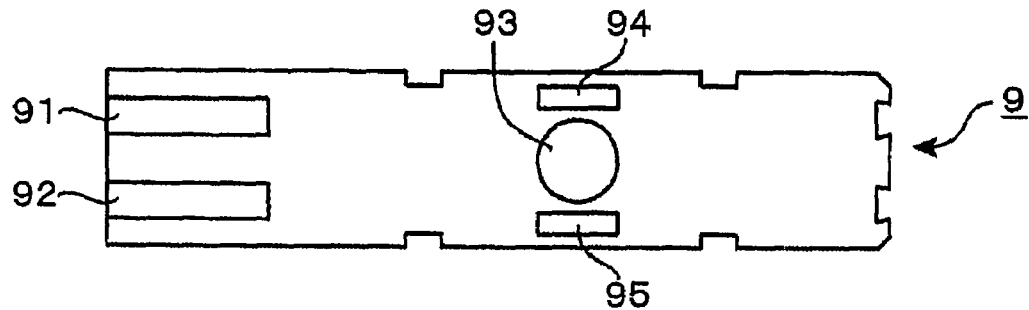
FIGS. 9A, 9B, 9C and 9D are assembly flow charts of the quartz sensor using the above-described quartz holding member.
Figure 9B:
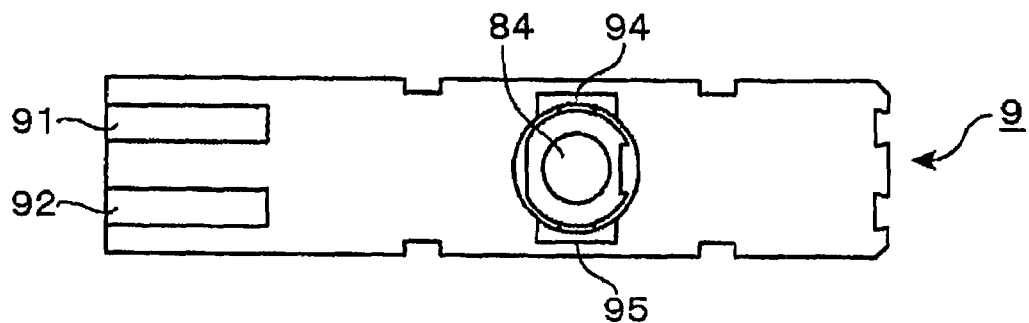

Another embodiment of the present invention will be explained next. FIGS. 8A, 8B and 8C shows the ring-shaped quartz holding member 8 used in the quartz sensor relating to the present embodiment. The quartz holding member 8 is made of an elastic material such as rubber, and composed of a table 81 on one side for placing the quartz resonator and a fitting portion 82 on the other side to be fitted into the substrate 9. The table 81 has a through hole 84 formed in the center, having the same size as or a little larger than the excitation electrode 22 of the quartz resonator 2. The table 81 also includes a ring-shaped table surface 84a of which external size is nearly the same as the quartz resonator 2, and a peripheral wall 80 surrounding the periphery of this 84a. On the upper surface portion of the peripheral wall 80, notches 84b and 85 are formed at the positions facing each other. Between the notches 84b and 85 on the upper surface, a projected piece 88 projecting inward is formed via a gap from the table surface 84a corresponding to the thickness of the quartz piece 21 is formed. The internal surface facing the projected piece 88 in the peripheral wall 80 is formed straight so as to match with a straight portion in a portion of the periphery of the quartz piece 21. The fitting portion 82 is arranged in the center on the opposite side to the table surface 84a in the table 81, and formed to have an outer dimension able to be inserted into a through hole 93 (refer to FIG. 9A) which is a hole of the circuit board (for instance, printed circuit board) 9 which will be described later. The fitting portion 82 includes a ring 86 with a length corresponding to the thickness of the circuit board 9; and a flange 87 formed on the top periphery of the ring 86. The inside space of the ring 86 is connected to the through hole 84.

Figure 9C:
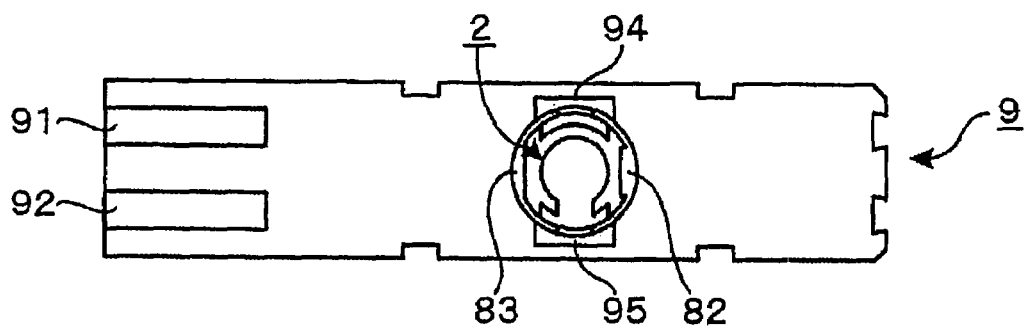
Figure 9D:
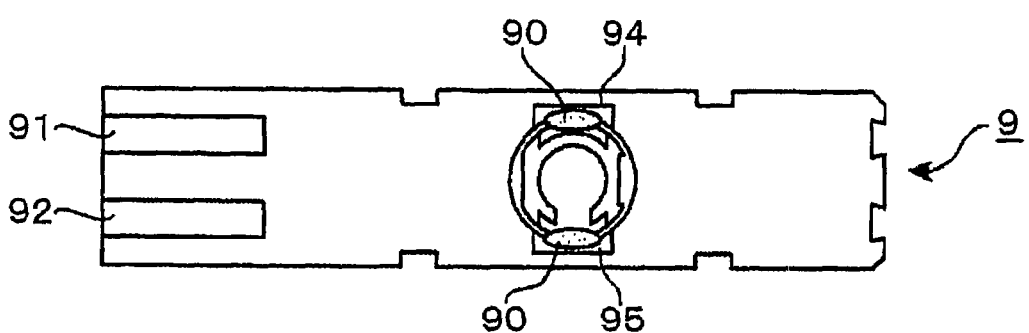

FIGS. 9A, 9B, 9C and 9D shows a circuit board 9 used in the present embodiment and the assembly process thereof. The circuit board 9 is provided with connecting terminals 91 and 92 composed of a printed circuit on one end side. These connecting terminals are detachable from the measuring device main unit 6 similarly to the previous embodiment. In the center of the circuit board 9, a round through hole 93 in a size corresponding to the outside shape of the ring 86 of the quartz holding member 8 is drilled, the flange 87 is engaged with the other surface side of the circuit board 9 by inserting the ring portion 86 into the through hole 93 from one surface side of the circuit board, so that the quartz holding member 8 is fixed to the circuit board 9. Thereafter, the quartz resonator 2 is fitted into the table 81 by lifting slightly the projected piece 82 of the table 81. FIG. 8C and FIG. 9C are plan views showing a state that the quartz resonator 2 is fitted into the table 81.

Figure 10A:
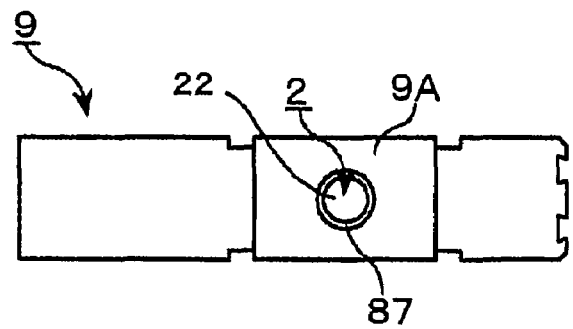
FIGS. 10A, 10B, 10C and 10D are assembly flow charts of the quartz sensor using the above-described quartz holding member.
Figure 10B:
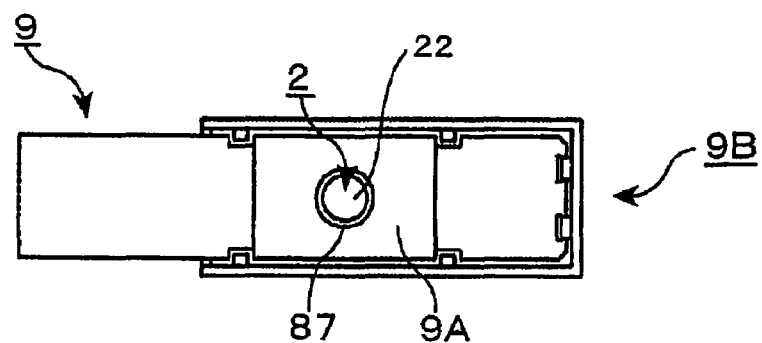
Figure 10C:
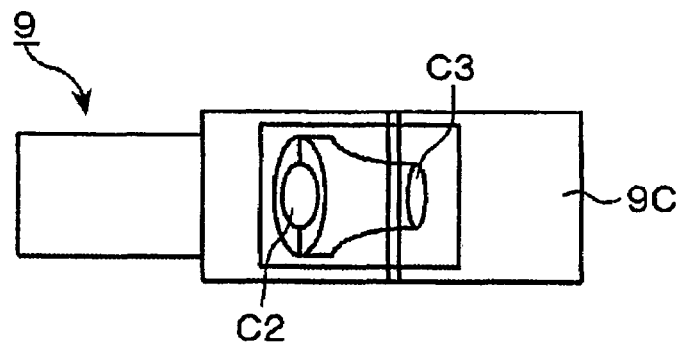
Figure 10D:
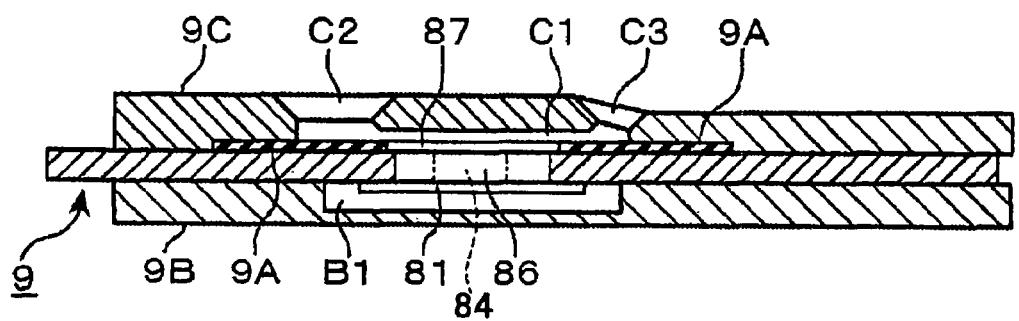

Furthermore, the electrodes (the derivation electrodes 24 and 25 in this embodiment) of the quartz resonator 2 and electrodes 94 and 95 of the circuit board 9 are connected by a conductive adhesive 90 via the notches 84b and 85 respectively. The electrodes 94 and 95 are electrically connected to the connecting terminals 91 and 92 respectively. Then, as shown in FIG. 10A, an elastic sheet, for instance, a rubber sheet 9A is overlaid on the other side of the circuit board 9 so that the through hole 93 formed in the center thereof and the quartz resonator 2 are put on top of each other, and an upper case 9C serving as a lid is further put on this sheet 9A so that the periphery of the upper case 9C is engaged with the periphery of the circuit board 9 (FIG. 10C). A pouring space C1, a pouring opening C2, a confirmation opening C3 connecting to this pouring space are formed on the upper case 9C as in the previous embodiment. A lower case 9B serving as a base support is mounted on one surface side of the circuit board 9 (FIG. 10B). A recess B1 is formed at a position corresponding to the table 81 in the lower case 9B as shown in FIG. 10D, and a space in the recess B1 forms an airtight space coming into contact with one surface side of the quartz resonator 2. Accordingly, a Langevin type quartz sensor is structured also in this embodiment.

The quartz sensor assembled in this way has a structure such that the one surface side of the quartz resonator 2 comes into contact with the housing area of a sample solution via the ring hole 84 of the quartz holding member 8, which makes it possible to conduct measurement similarly to the previous embodiment. In this embodiment also, as shown by FIG. 10D, the other surface side of the quartz resonator 2 faces an opposing surface portion in a size larger than the quartz resonator 2 of the upper case 9C via the housing area. In other words, the excitation electrode 22 of the quartz resonator 2 faces the first area mentioned in the basic structure of the principal portion. Since the front and behind of the first area are adjacent to areas is corresponding to the second and third areas described in the basic structure of the principal portion, it is possible in the present embodiment also to conduct the measurement by oscillating the quartz resonator 2 in a state that the influence of the surface tension of a sample solution is suppressed during the measurement.

Figure 11:
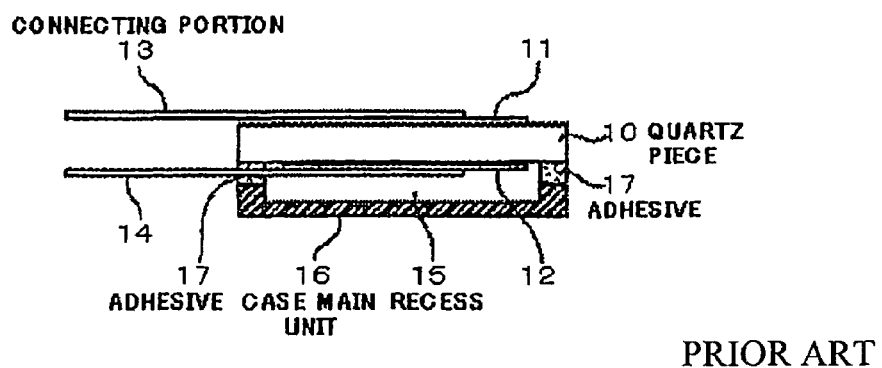
FIG. 11 is an explanatory view showing a structural example of a conventional quartz sensor.
Figure 12A:
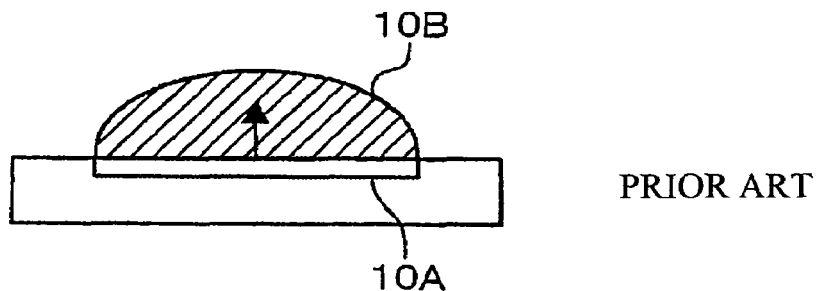
FIG. 12 is an explanatory view showing the influence of the surface tension on the quartz resonator which is equipped in the above-described quartz sensor.
Figure 12B:
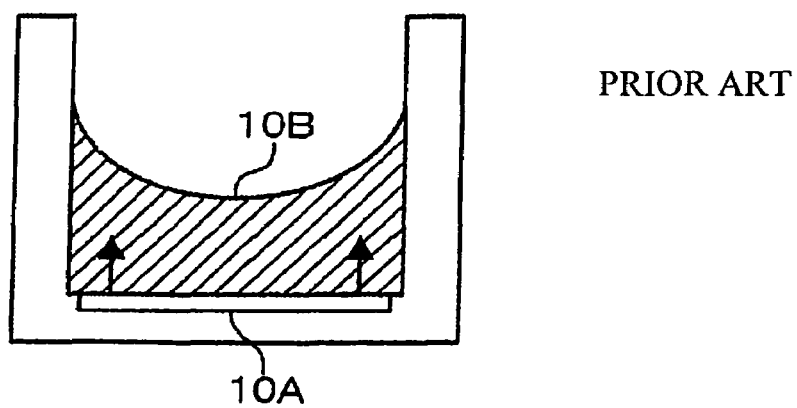

In the above embodiment, the inventor prepared a structure shown in FIG. 11 using a quartz resonator having the natural frequency of 30 MHz, and tried to oscillate by pouring 200 μL of purified water, but it did not oscillate. On the contrary, when the same sample solution is poured into the quartz sensor described in the first embodiment which uses a similar quartz resonator, it oscillates in a stable fashion.

The invention claimed is:

1. A quartz sensor used for measuring an object to be measured in a sample solution, comprising:
   a member provided with a recess for forming an airtight space;
   a quartz resonator held by said member in a state that excitation electrodes are equipped respectively on one surface side and the other surface side of a quartz piece of the quartz resonator and the excitation electrode on the other surface side covers the recess so as to face said airtight space;
   an adsorbing layer which is provided on the excitation electrode on said one surface side, and adsorbs the object to be measured in the sample solution;
   a housing area forming portion which encloses the upper space above the one surface side of said quartz resonator and for forming the housing area of the sample solution;
   an opposing surface portion which faces the one face side of said quartz resonator via said housing area and is larger than the excitation electrode of the quartz resonator;
   a pouring opening which is formed in the outside area of the opposing surface portion and for pouring the sample solution into said housing area, said pouring opening being formed at a position higher than said opposing surface portion;
   a confirmation opening connected to said housing area at a position different from said pouring opening, and for confirming a liquid level of the sample solution; and
   wherein the object is measured based on the variation in the natural frequency of the quartz resonator caused by adsorption of the object to be measured on an adsorbing layer, and the measurement is conducted in a standstill state that the sample solution is filled in the lower side of the opposing surface portion.

2. The quartz sensor according to claim 1, wherein the equivalent thickness of said quartz piece is thinner than 200 μm.

3. A sensing device, comprising:
a quartz sensor described in claims 1 or 2; and
a measuring device main unit determining the presence of the object to be measured or the concentration thereof by detecting the variation in the natural frequency of the quartz sensor.

4. A sensing device, comprising:
a quartz sensor described in claims 1 or 2; and
a measuring device main unit determining the absence of the object to be measured or the concentration thereof by detecting the variation in the natural frequency of the quartz sensor.

5. A sensing device, comprising:
a quartz sensor described in claims 1 or 2; and
a measuring device main unit determining the presence and absence of the object to be measured or the concentration thereof by detecting the variation in the natural frequency of the quartz sensor.

* * * * *